United States Patent
Bönström et al.

(10) Patent No.: US 10,607,067 B2
(45) Date of Patent: Mar. 31, 2020

(54) FITNESS DEVICE AND METHOD FOR AUTOMATICALLY CHECKING FOR THE CORRECT PERFORMANCE OF A FITNESS EXERCISE

(71) Applicant: PIXFORMANCE SPORTS GMBH, Berlin (DE)

(72) Inventors: Valerie Bönström, Berlin (DE); Niclas Bönström, Berlin (DE)

(73) Assignee: PIXFORMANCE SPORTS GMBH, Berlin (DE)

( * ) Notice: Subject to any disclaimer, the term of this patent is extended or adjusted under 35 U.S.C. 154(b) by 962 days.

(21) Appl. No.: 14/378,619

(22) PCT Filed: Feb. 14, 2013

(86) PCT No.: PCT/EP2013/052970
§ 371 (c)(1),
(2) Date: Aug. 13, 2014

(87) PCT Pub. No.: WO2013/120951
PCT Pub. Date: Aug. 22, 2013

(65) Prior Publication Data
US 2015/0039106 A1    Feb. 5, 2015

(30) Foreign Application Priority Data
Feb. 14, 2012    (DE) .................. 10 2012 101 152

(51) Int. Cl.
*A63F 9/24*    (2006.01)
*G06K 9/00*    (2006.01)
(Continued)

(52) U.S. Cl.
CPC ..... *G06K 9/00342* (2013.01); *G06F 19/3481* (2013.01); *G09B 19/0038* (2013.01)

(58) Field of Classification Search
CPC ........ A63B 24/0062; A63B 2024/0015; G06F 3/011; G06F 3/017; G06F 3/0304
See application file for complete search history.

(56) References Cited

U.S. PATENT DOCUMENTS

| 5,791,351 A | 8/1998 | Curchod |
| 6,416,327 B1 | 7/2002 | Wittenbecher |
(Continued)

FOREIGN PATENT DOCUMENTS

| DE | 29720110 U1 | 1/1998 |
| DE | 298 20 134 U1 | 5/1999 |
(Continued)

OTHER PUBLICATIONS

JP Office Action dated Nov. 22, 2016 as received in Application No. 2014-556108 (English Translation).
(Continued)

*Primary Examiner* — David L Lewis
*Assistant Examiner* — Eric M Thomas
(74) *Attorney, Agent, or Firm* — Maschoff Brennan

(57) ABSTRACT

A stationary fitness device for set-up in a fitness studio is provided. The stationary fitness device comprises a sensor equipment for the contactless detection of the motions of a user of the fitness device and for forwarding signals generated by the sensor equipment on the basis of the motions of the user, a display unit for displaying motion sequences of a fitness exercise by a virtual fitness trainer and for displaying a virtual image of the user, a computer unit which on the basis of the signals received from the sensor equipment generates the virtual image of the user and displays the same by means of the display unit, and an identification means for identifying a particular user from a list of users stored in the computer unit. The computer unit is equipped and provided to display motion sequences of a fitness exercise stored in a (Continued)

memory of the computer unit for the identified user by the virtual fitness trainer by means of the display unit, perform a comparison with reference to the received signals concerning the extent to which the detected motions performed by the user for the fitness exercise deviate from the motion sequences stored in a memory of the computer unit and displayed by the virtual fitness trainer, and display to the user a deviation of the motions performed by the user from the stored motion sequences by means of the display unit.

14 Claims, 2 Drawing Sheets

(51) Int. Cl.
　　*G06F 19/00*　　(2018.01)
　　*G09B 19/00*　　(2006.01)

(56) References Cited

U.S. PATENT DOCUMENTS

| | | |
|---|---|---|
| 7,887,460 B2 | 2/2011 | Maschke |
| 2003/0054327 A1 | 3/2003 | Evensen |
| 2007/0219051 A1 | 9/2007 | Hayashino et al. |
| 2010/0280418 A1 | 11/2010 | Klose |
| 2011/0302293 A1 | 12/2011 | Buban |
| 2012/0183939 A1* | 7/2012 | Aragones ........... A63B 24/0006 434/247 |
| 2012/0183940 A1* | 7/2012 | Aragones ............ G06F 19/3437 434/247 |
| 2012/0308140 A1* | 12/2012 | Ambrus ............. G06K 9/00362 382/190 |

FOREIGN PATENT DOCUMENTS

| | | |
|---|---|---|
| DE | 10 2005 018 634 A1 | 10/2006 |
| DE | 10 2009 002 747 A1 | 11/2010 |
| EP | 2402061 A1 | 1/2012 |
| JP | 2003-245389 A | 9/2003 |
| JP | 2005-111178 A | 4/2005 |
| JP | 2007-181528 A | 7/2007 |
| JP | 2007-236545 A | 9/2007 |
| JP | 2010-069102 A | 4/2010 |
| WO | 97/29814 A1 | 8/1997 |
| WO | 2012061804 A1 | 5/2012 |

OTHER PUBLICATIONS

German Opposition document filed in corresponding application 10 2012 101 152.4 dated Sep. 30, 2015.

* cited by examiner

FITNESS DEVICE AND METHOD FOR AUTOMATICALLY CHECKING FOR THE CORRECT PERFORMANCE OF A FITNESS EXERCISE

CROSS-REFERENCE TO A RELATED APPLICATION

This application is a National Phase Patent Application of International Patent Application Number PCT/EP2013/052970, filed on Feb. 14, 2013, which claims priority of German Patent Application Number 10 2012 101 152.4, filed on Feb. 14, 2012.

BACKGROUND

The present invention relates to a stationary fitness device for set-up in a fitness studio as well as to a system comprising a plurality of fitness devices and to a method for automatically checking for the correct performance of a fitness exercise.

The fitness device according to the invention expands fitness devices known so far, as they are usually set up in fitness studios, by an automated, electronic check as to whether a user correctly performs a fitness exercise to be performed at the fitness device. In fitness devices used so far the problem exists that a fitness exercise only can be checked by a personal fitness trainer and hence there regularly is a risk that an exercise is not performed correctly in the absence of the fitness trainer. This can possibly lead to injuries of the user or at least considerably reduce the effectiveness of the fitness exercise to be performed.

In fitness devices known so far, i.e. in particular usual fitness devices to be found in a conventional fitness studio, much effort therefore regularly is taken, in order to avoid a maloperation and to permit usage of the device only in a certain position of the user. Experience shows, however, that this is possible only with individual fitness exercises. The correct performance of the majority of fitness exercises depends on the fact that in a fitness studio a sufficient number of fitness trainers or a fitness trainer personally responsible for the user constantly checks the posture and the motion sequences of the user of the fitness device and reminds him of possible false postures or wrong uses.

In addition, up to now it regularly only is possible for users of a fitness device to subjectively detect the correct performance of a fitness exercise and write down possible training successes and only afterwards possibly enter the same into a database and have them evaluated.

SUMMARY

Accordingly, it is an object underlying the present invention to provide a possibility for better monitoring fitness exercises to be performed at a fitness device for their correct performance and for quickly and easily adapting the fitness exercises to be performed at a fitness device to a certain user or type of user.

The stationary fitness device according to an exemplary embodiment of the invention is formed and provided for set-up in a fitness studio and is equipped with several electronic components, including a sensor equipment for the contactless detection of the motions of a user of the fitness device and for forwarding signals generated by the sensor equipment on the basis of the motions of the user, a display unit for displaying motion sequences of a fitness exercise by a virtual fitness trainer and for displaying a virtual image of the user, a computer unit which on the basis of the signals received from the sensor equipment generates the virtual image of the user and displays the same by means of the display unit, and an identification means for identifying a particular user from a list of users stored in the computer unit.

The computer unit is equipped and provided to display motion sequences of a fitness exercise stored in a memory of the computer unit for the identified user by the virtual fitness trainer by means of the display unit, perform a comparison with reference to the signals received from the sensor equipment concerning the extent to which the detected motions performed by the user for the fitness exercise deviate from the motion sequences stored in a memory of the computer unit and displayed by the virtual fitness trainer, and display to the user (in real time) a deviation of the motions performed by the user from the stored motion sequences by means of the display unit.

A user of the fitness device hence receives a direct feedback in real time via the display unit to what extent the fitness exercise demonstrated by the virtual fitness trainer previously or at the moment is carried out correctly. In conjunction with the computer unit and the sensor equipment, the display unit thus supplies a virtual image of the user currently performing the fitness exercise in real time and provides the same to the user with an information as to whether the fitness exercise demonstrated by the virtual fitness trainer is carried out correctly and how much the motion currently carried out by the user possibly deviates from the specified motion sequence.

For this purpose, the representation of the virtual fitness trainer can be superimposed with the virtual image of the user and the superimposed representation can be played back by the user by means of the display unit during the performance of the fitness exercise, in order to visualize possible deviations of the motions of the user from the specified motion sequences. Another suitable possibility is to separately display the virtual fitness trainer and e.g. mark the body parts of the user deviating from the ideal position in other colors than those which are at the correct position. The user looking at the display unit thus sees his virtual image together with the virtual fitness trainer and a real-time indication of how far his motions correspond with the (desired) motion sequence specified by the fitness exercise.

In a preferred design variant the computer unit furthermore is equipped and provided to store the extent of the deviations—and hence also the efficiency of the fitness exercise performed—and to (electronically) provide the same to the user as readable data. For example, directly subsequent to the performance of a fitness exercise, a user thus can obtain an evaluation as to how good he was in performing the fitness exercise. In this way, a personalized training plan—possibly automatically—also can be created, processed and/or output (electronically) by the fitness device. The data provided by the fitness device thus give a direct feedback to the user as to whether the fitness exercise has been performed correctly and how efficiently.

The sensor equipment and the computer means preferably are equipped and provided to identify deviations of the motions performed by the user from the stored motion sequences with reference to the body posture of the user. The evaluation of the extent to which a specified fitness exercise has been carried out correctly hence is not effected here (alone) on the basis of the speed with which a user executes a fitness exercise demonstrated by the virtual fitness trainer. The evaluation rather includes the body posture of the user during the performance of the fitness exercise and hence for example in particular the orientation of the arms and legs of the user. Hence it regularly is of minor importance for the training success, whether a fitness exercise has been carried out with sufficient speed. What is distinctly more relevant is the maintenance of certain positions during the motion sequence performed. In a preferred design variant it therefore depends on the correspondences with the specified body posture or the specified body postures to what extent the fitness device classifies the performance of the fitness exercise as correct.

In one exemplary development it furthermore can be provided that the computer unit is equipped and provided to record and store the motion sequences of the user detected during the performance of the fitness exercise, so that subsequent to the performance of the fitness exercise a recorded video with the virtual image of the user can again be played back by means of the display unit. In this video, the virtual fitness trainer and possible deviations from the specified motion sequences can of course also have been recorded. It hence is possible for the user to not only be informed of the training success in real time during the fitness exercise, but also to again analyze his performance of the fitness exercise at a later date—for example in a personal meeting with a real fitness trainer.

In one design variant the fitness device is equipped and provided to record and digitize a fitness exercise carried out by a real fitness trainer, so that the fitness exercise can be played back by the virtual fitness trainer by means of the display unit. The fitness device thus is capable here of carrying out a so-called motion capture method in which motions of a real person—here the real fitness trainer—are recorded and converted into digitally processable signals. The recording of a fitness exercise by the real fitness trainer can be effected for a plurality of different users or specifically for exactly one particular user. For example, during a first use of the fitness device a real fitness trainer can demonstrate the performance of a fitness exercise to the user and in doing so have himself detected by the sensor equipment of the fitness device, so that subsequent to the performance of the fitness exercise a virtual image of the fitness trainer is available, which during the subsequent performance of the same fitness exercise by the user can be utilized for checking the motion sequences.

In this connection it can also be provided that in a database of a system electronically coupled with the fitness device several personalized fitness exercises to be demonstrated by a virtual fitness trainer were recorded and stored for each user to be identified by the fitness device. In this way, a set of personalized fitness exercises is provided for a particular user, from which the user selects a fitness exercise to be performed, when logging in (manually or automatically) at the fitness device.

In one exemplary embodiment it is preferred that the fitness device includes a communication equipment by means of which data of a user can be transmitted to the computer unit. In particular, it can be provided that a personal fitness plan of the identified user is transmittable to the computer unit. This should mean in particular that for example via the Internet or an interface at the fitness device a user can transmit a customized fitness plan or a fitness plan prepared by himself with a certain number of fitness exercises to the fitness device, so that the fitness device displays a fitness exercise customized to the user by the virtual fitness trainer by means of its display unit.

It can of course also be provided that via an input device at the fitness device data specific for the respective user can be entered, such as for example his weight, his size, his age, etc.

There can also be provided a communication equipment provided at the fitness device, which is able to store the user data relevant for the respective user, including his personal fitness plan, on a central server or a storage medium of the user removable from the fitness device. The user of a fitness device according to the invention, which is developed in this way, thereby is enabled to easily perform the customized fitness exercises at another fitness device. In particular, this includes the possibility of having his user data available at a fitness device which is located in another town than the device otherwise preferred by the user in the fitness studio of his place of residence.

It can also be provided that the data on one fitness exercise or several fitness exercises as provided by the fitness device also can be utilized by other IT terminals, such as PCs, games consoles or mobile phones including so-called smart phones. A user of the fitness device thus is enabled to perform the fitness exercises contained in his fitness plan and possibly demonstrated by his personal virtual fitness trainer also without the stationary fitness device.

In addition, it hence becomes possible that for example fitness exercises to be downloaded via an online platform can be transmitted to the computer unit of a fitness device according to the invention. Thus, for example real fitness trainers can provide fitness exercises recorded and digitized by them at a fitness device, which can be utilized by a user at the same or another fitness device in the fitness studio of his choice. By the sensor unit provided according to the invention it is checked in real time whether the user correctly performs the corresponding fitness exercise, without the user having to be accompanied by a real fitness trainer.

In one exemplary embodiment, the fitness device is provided with an identification means which identifies a user by means of an entered user ID and a password and/or by means of a contactless scanning of an identification element carried by the user. The identification element for example can be a transponder whose unique identifier is automatically read out by a reader of the identification means, when the user approaches the fitness device and/or stays at the same. The fitness device for example can be equipped with a so-called RFID system. "RFID" stands for the English technical term "radio frequency identification" (identification by means of electromagnetic waves). However, the identification of a user is of course also possible by other known contactless transmission devices.

In a particular embodiment of the invention, a plurality of fitness devices—preferably coupled with each other—provides a system in which the individual fitness devices each are equipped to direct an identified user after termination of a fitness exercise performed at a first fitness device to a second fitness device, at which a succeeding fitness exercise is to be performed by the user. Via the display unit, a user for example is informed at which (other) fitness device he should perform which succeeding fitness exercise. This is expedient in particular when different fitness machines can be used at different fitness devices.

The individual fitness devices preferably are electronically—e.g. via a radio or cable network—coupled with each other, so that data on an identified user, who has performed a fitness exercise at the first fitness device, are available at the second fitness device.

To optimize and individualize the efficiency of the individual fitness exercises to be performed for the individual user, the system advantageously is equipped to automatically perform an assignment to the second fitness device—and preferably also the kind of fitness exercise to be performed at the same—in dependence on
- a determined extent of the deviations of the motions performed by the user from the stored motion sequences during the fitness exercise at the first fitness device and/or
- the identified user and/or
- fitness data of the identified user, in particular the blood pressure and/or the heart rate.

For example with reference to the determined success with which a user has completed a preceding fitness exercise or several preceding fitness exercises and an individual training plan for the respective user, the system thus can inform the user of the succeeding fitness exercise and the fitness device at which this fitness exercise is to be performed. For this automatic assignment to the succeeding fitness device it is also possible, for example, to evaluate fitness data of the user currently measured during the fitness exercise performed last, such as the heart rate and the blood pressure.

In one variant, it is also possible to evaluate fitness data which were each measured during one of several fitness exercises performed previously. The system for example is equipped to evaluate a course of the fitness data over several fitness exercises carried out previously and specify different sequences of fitness exercises for the user in dependence on the course. It can be recommendable, for example, to subsequently assign a less exhausting fitness exercise to the user, when during the fitness exercise performed last a comparatively high heart rate was detected, although the user has not performed the fitness exercise correctly and major deviations from the specified motion sequences were detected via the respective fitness device.

Furthermore, the fitness devices in a system according to the invention can be arranged such that each fitness device forms an individual station of a circuit training for an identified user. In such system several fitness devices each with one display unit, one sensor equipment and one computer unit hence are arranged one beside the other—e.g. substantially along a circular path. Each individual fitness device then shows a fitness exercise of a circuit training to be performed by the identified user. When the user moves on from one fitness device to the next fitness device, the next fitness device is switched on automatically—for example due to a contactless identification means—and/or activates the fitness program provided for the user with the virtual fitness trainer demonstrating the corresponding fitness exercise.

In one development it can also be provided that the system is equipped to not only inform the user of the assignment to the next fitness device, but at the same time also reserve the assigned fitness device for the respective user. The next fitness device provided for the respective user and not used so far hence cannot be used by another user—e.g. during a set time period—, so that the user to which the fitness device has been assigned can move on to the same without waiting times. When all fitness devices of the system currently are occupied by the user, it can be provided that the system generates an assignment list for each fitness device, in which an order of the waiting users is fixed.

According to a further aspect of the present invention, there is proposed a method for automatically checking for the correct performance of a fitness exercise.

In accordance with the preceding explanations, this method is characterized by the following:
- providing a fitness device with at least one sensor equipment, one display unit and one computer unit,
- recording and digitizing a fitness exercise performed by a real fitness trainer (in a motion capture method), so that the fitness exercise can be played back by a virtual fitness trainer by means of the display unit,
- displaying motion sequences of the recorded and digitized fitness exercise by the virtual fitness trainer by means of the display unit of the fitness device,
- contactless detection of the motions of a user utilizing the fitness device by means of the sensor equipment and on the basis of the motions of the user forwarding signals generated by the sensor equipment to the computer unit,
- generating a virtual image of the user by the computer unit on the basis of the signals received from the sensor equipment and displaying the virtual image of the user by means of the display unit in real time,
- performing a comparison with reference to the signals received from the sensor equipment by the computer unit concerning the extent to which the detected motions performed by the user for the fitness exercise deviate from the motion sequences stored in a memory of the computer unit and demonstrated by the virtual fitness trainer, in order to check for the correct performance of the fitness exercise by the user, and
- displaying deviations of the motions performed by the user from the stored motion sequences by means of the display unit in real time for the user performing the fitness exercise.

What is essential here on the one hand is the recording and digitization of fitness exercises performed by a real fitness trainer or a real person, in order to have the recorded motion sequences demonstrated by a virtual fitness trainer, and on the other hand the matching with the motions performed by a user, in order to inform the user in real time of possible deviations (and consequently also correspondences) of the motions performed by him with the (desired) motion sequences specified by the virtual fitness trainer.

BRIEF DESCRIPTION OF THE DRAWINGS

Further advantages and features of the present invention will become apparent from the following description of an exemplary embodiment with reference to the Figures.

DETAILED DESCRIPTION

Figure 1:
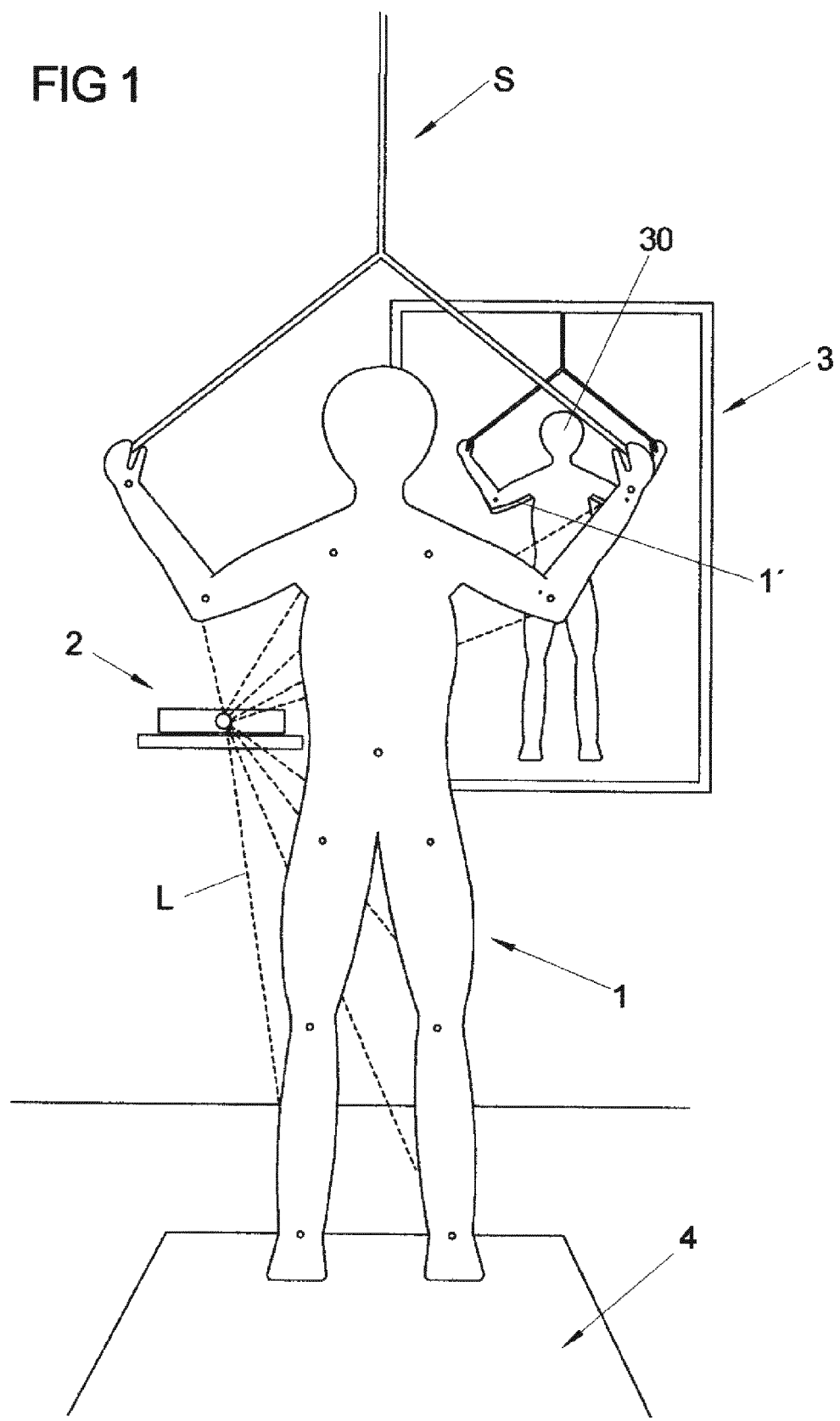
FIG. 1 schematically shows a design variant of a fitness device according to the invention, which is also suitable for performing the method according to the invention.

FIG. 1 schematically shows an exemplary embodiment of a fitness device according to the invention. This fitness device comprises a display unit 3 with a monitor or screen, an optical sensor equipment 2 and a computer unit not shown here in detail. The computer unit is coupled both with the sensor equipment 2 and with the display means 3 and in the present case accommodated in the same housing as the sensor equipment 2.

A user 1 present on a training area 4 is scanned via detection beams L emitted by the sensor equipment 2, in order to optically detect the motions carried out by the user 1 when performing a fitness exercise and to provide the same on a display of the display unit 3 for generating a virtual image 1' of the user 1. The virtual image 1' of the user 1 is generated by means of the computer unit by electrical signals generated by the sensor equipment and output on the display of the display unit 3. For this purpose, the computer unit includes at least one processor, in order to generate image data for the virtual image 1' from the signals of the optical sensor equipment 2.

The computer unit here furthermore is equipped and provided to display fitness exercises to be carried out by the user 1 on the display unit 3 by a virtual fitness trainer 30. At the same time, the computer unit monitors the extent to which the motions carried out by the user 1 correspond with the stored motion sequences of the virtual trainer 30 and informs the user 1 of possible deviations by a suitable representation (e.g. superposition of his virtual image 1' with the virtual fitness trainer 30 or different colors for body parts deviating from or matching with the ideal position).

In the present case, the fitness device includes a firmly installed sports equipment S which can or even must be utilized by the user 1 for performing a specified fitness exercise. However, it is of course possible that via the virtual fitness trainer 30 a fitness exercise is demonstrated to the user 1, which can do without a sports equipment S.

In the present case, the virtual fitness trainer 30 was created by the computer unit of the fitness device or a known recording device on the basis of recorded motions of a real fitness trainer. The recorded motions of the real fitness trainer were digitized, in order to generate the virtual image of the fitness trainer or the virtual fitness trainer 30 and be able to evaluate to what extent the motions of the user 1 detected by the sensor equipment 2 correspond with the specified motions of the virtual fitness trainer 30. Checking for the correct performance of a specified fitness exercise, which is possible thereby, is effected in real time, so that the user 1 looking at the display of the display unit 3 immediately or at least only with a minor delay gets a feedback as to whether he correctly performs a specified fitness exercise.

In the present case, the fitness device is equipped with an identification means which in a contactless manner detects when a user 1 is present on the training area 4. In addition, it is provided with a reader for the contactless scanning of an identification element carried by the user, such as for example an RFID transponder.

The illustrated fitness device can execute the following functions:

1. The fitness device is equipped and provided to indicate to the user 1 his personal fitness plan via the display unit 3. In particular, this includes the data for the fitness exercise to be performed, which each are customized to the user 1, such as for example the number of repetitions, the weight to be used, or previous training successes at the respective fitness device or during the fitness exercise to be performed subsequently.

2. At each fitness device a personalized, virtual fitness trainer 30 can demonstrate to the user 1 the optimum performance of a fitness exercise. Via the sensor equipment 2, this demonstration can have been digitized and stored for the respective user 1, for example on a central server.

3. Via the display unit 3, there can be provided an animated 3D visualization of the correctly performed fitness exercise according to the fitness plan selected by the user 1 or stored for the user 1 at the fitness device. Accordingly, the correct performance of the fitness exercise for example also can be demonstrated to the user 1 with detailed instructions by the 3D-animated virtual fitness trainer 30. Alternatively or in addition a standardized program, which hence is not individually adapted to the user 1, can be selected and demonstrated by the virtual fitness trainer 3, wherein this standardized fitness program and the included fitness exercises are compiled by the computer unit or a program stored therein from the personal data of the user 1 (such as age, size and weight), which are detected by the fitness device or stored therein.

4. Via the sensor equipment 2, the performance of the fitness exercise by the user is monitored and a 3D-animated virtual image 1' of the user 1 is displayed on the display unit 3 in real time.

5. The signals supplied by the sensor equipment 2 are evaluated by an algorithm provided on the computer unit, and it is analyzed to what extent the motions performed by the user 1 correspond with the motion sequence specified by the virtual fitness trainer 30. Possible deviations are displayed on the display of the display unit 3 in real time and can be viewed once again even after termination of the fitness exercise.

6. In the present case, all user-relevant digital data including the personal fitness plan are stored on a central server. This permits the utilization of the user data on different IT input devices, such as PCs, games consoles or mobile phones, so that a user 1 can retrieve, view and process his personal fitness plan also independent of the fitness device and can execute his fitness plan by means of another machine or another fitness device. Furthermore, the fitness device or a system of fitness devices can be provided with a communication equipment, in order to be able for example to transmit data retrievable from the Internet to a computer unit of the fitness device. It can be provided, for example, that a fitness device can access to an online platform on which different real fitness trainers in turn provide fitness exercises created and digitized by them with a virtual image which can be utilized by a user 1.

Alternatively or in addition, a communication equipment of the fitness device can be suitable for communicating with a storage medium of the user 1, in order to be able to access data stored thereon, which can be utilized for generating and displaying a virtual fitness trainer 30 on the display of the display unit 3.

Figure 2:
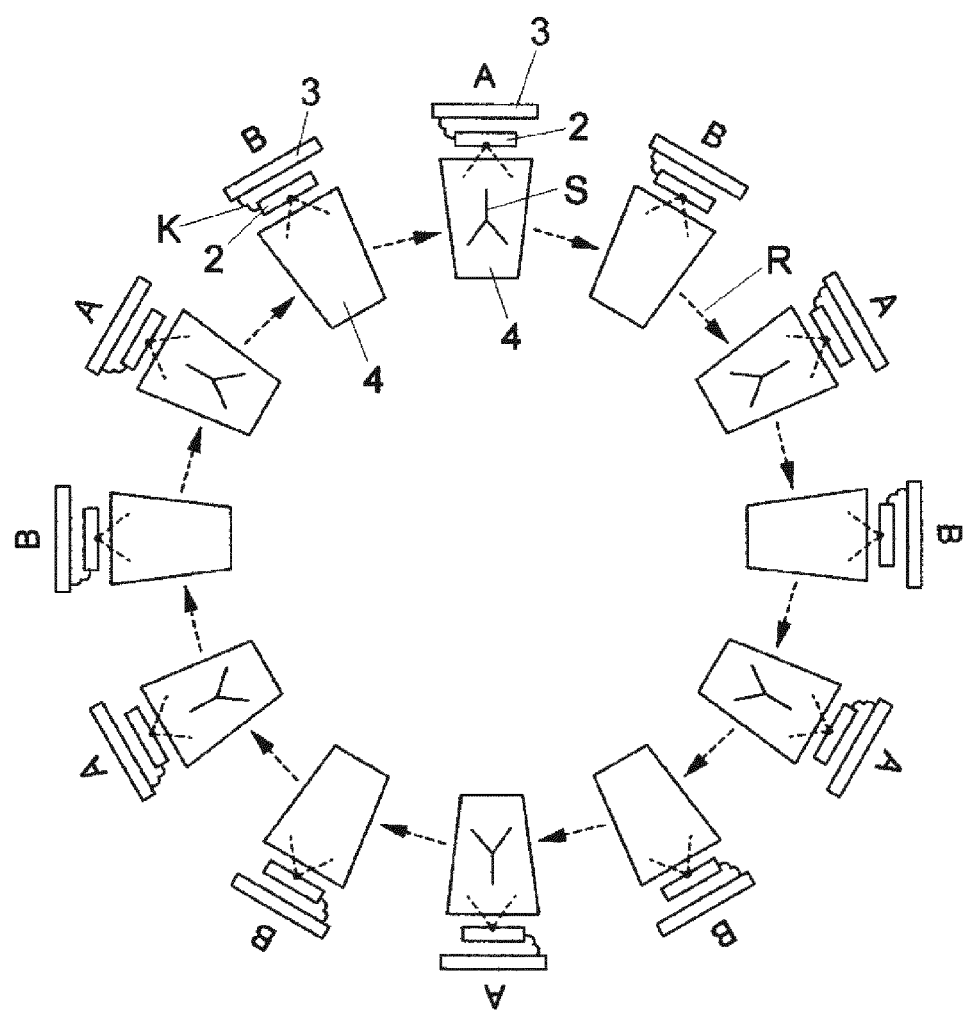
FIG. 2 schematically shows a system of several fitness devices according to FIG. 1, which are arranged as individual stations of a circuit training.

FIG. 2 schematically illustrates a system with a plurality of fitness devices corresponding to FIG. 1, wherein the individual fitness devices are arranged and coupled with each other such that each fitness device forms an individual station of a circuit training At each of the fitness devices, a user 1 correspondingly performs a fitness exercise displayed on the respective display unit 3 and then moves on to the next fitness device along a training direction R.

In the Figure, the individual fitness devices which here are designated with "A" and "B" merely differ in whether or not the use of a sports equipment S is intended. Otherwise, the individual fitness devices are formed identical to each other and here as well are equipped with a sensor equipment 2 and a computer unit integrated into the same housing, which is connected with the display unit 3 via a cable K. Via an identification element carried by the user 1, such as for example an RFID transponder, each of the fitness devices is capable of identifying the user via its respective identification means when the user moves on from one fitness device to the next fitness device, and to display the fitness exercise provided for him in the course of the circuit training via a virtual fitness trainer 30 on the respective display in the display unit 3.

After termination of a fitness exercise performed at a first fitness device A, an identified user 1 can be directed to a second fitness device A or B, at which a succeeding fitness exercise is to be performed by the user 1. Via the respective display unit 3, a user 1 for example is informed via the respective display unit 3, at which other fitness device A or B he should perform which succeeding fitness exercise.

To optimize and individualize the efficiency of the individual fitness exercises to be performed for the individual user, the system here can be equipped to automatically perform an assignment to the second fitness device—and preferably also the kind of fitness exercise to be performed at the same—in dependence on
- a determined extent of the deviations of the motions performed by the user 1 from the stored motion sequences during the fitness exercise at the first fitness device A or B and/or
- the identified user 1 and/or
- fitness data of the identified user, e.g. the blood pressure and the heart rate.

For example with reference to the determined success with which a user 1 has completed a preceding fitness exercise or several preceding fitness exercises and an individual training plan for the respective user, the system thus can inform the user of the succeeding fitness exercise and the fitness device A or B at which this fitness exercise is to be performed. For this automatic assignment to the succeeding fitness device, fitness data of the user currently measured during the fitness exercise performed last, such as the heart rate and the blood pressure, preferably are evaluated here. The measured fitness data are transmitted to the system for example via a measuring device (e.g. via a chest strap) connected with the system—preferably wirelessly—and carried by the user. Each user here thus has his own measuring device which during the utilization of a fitness device A or B transmits fitness data to the system and/or the respective fitness device A or B. Alternatively, each fitness device can have its own measuring device which is applied or touched by a user, when he performs a fitness exercise at the respective fitness device A, B.

The solution according to the invention not only provides an automated check for the correct performance of a fitness exercise, but it also becomes possible for example that fitness exercises individually adapted to a user 1 are automatically visualized at a display unit 3 of a fitness device, when a user 1 approaches the fitness device and possibly stays at the fitness device within reach of a reader of the fitness device for a specified activation time (for example 1 to 2 sec.).

In one development it can also be provided that the system is equipped to not only inform the user 1 of the assignment to the next fitness device A or B, but at the same time also reserve the assigned fitness device A, B for the respective user 1. The next fitness device A, B to which the user 1 should move hence is exclusively available for this user 1—at least for a certain period.

LIST OF REFERENCE NUMERALS

1 user
1' virtual image of the user
2 sensor equipment
3 display unit
30 virtual fitness trainer
4 training area
K cable
L detection beam
R training direction
S sports equipment

The invention claimed is:

1. A stationary fitness device for set-up in a fitness studio, comprising
   a sensor equipment for the contactless detection of the motions of a user of the fitness device and for forwarding signals generated by the sensor equipment on the basis of the motions of the user,
   a display unit for displaying motion sequences of a fitness exercise by a virtual fitness trainer and for displaying a virtual image of the user,
   a computer unit which on the basis of the signals received from the sensor equipment generates the virtual image of the user and displays the same by means of the display unit,
   an identification means for identifying a particular user from a list of users stored in the computer unit, and
   a communication equipment by means of which data can be transmitted from a user to the computer unit, wherein a personal fitness plan of the identified user can be transmitted to the computer unit by means of the communication equipment and the computer unit is equipped and provided to demonstrate at least one fitness exercise by the virtual fitness trainer on the basis of the personal fitness plan by means of the display unit,
   wherein the computer unit is equipped and provided to
      display motion sequences of a fitness exercise stored in a memory of the computer unit for the identified user by the virtual fitness trainer by means of the display unit,
      perform a comparison with reference to the received signals concerning the extent to which the detected motions performed by the user for the fitness exercise deviate from the motion sequences stored in a memory of the computer unit and displayed by the virtual fitness trainer, and
      display to the user a deviation of the motions performed by the user from the stored motion sequences by means of the display unit,
   and wherein the communication equipment is further provided to store user-relevant data including the personal fitness plan on a central server or on a storage medium of the user removable from the fitness device so that the user can use the user-relevant data on different IT input devices independent of the fitness device and can retrieve, view, process and execute its personal fitness plan by means of an IT input device or another fitness device.

2. The fitness device according to claim 1, wherein the computer unit is equipped and provided to superimpose the representation of the virtual fitness trainer with the virtual image of the user and to play back the superimposed representation by means of the display unit, while the fitness exercise is performed by the user.

3. The fitness device according to claim 1, wherein the computer unit is equipped and provided to use the display unit for displaying when body parts of the user deviate from a position specified by the virtual fitness trainer, while the fitness exercise is performed by the user.

4. The fitness device according to claim 1, wherein the computer unit is equipped and provided to store the extent of the deviations and provide the same to the user as readable data.

5. The fitness device according to claim 1, wherein the sensor equipment and the computer unit are equipped and provided to identify deviations of the motions performed by the user from the stored motion sequences with reference to the body posture of the user.

6. The fitness device according to claim 1, wherein the computer unit is equipped and provided to record and store the motion sequences of the user detected during the performance of the fitness exercise, so that subsequent to the performance of the fitness exercise a recorded video with the virtual image of the user can again be played back by means of the display unit.

7. The fitness device according to claim 1, wherein the fitness device is equipped and provided to record and digitize a fitness exercise carried out by a real fitness trainer, so that the fitness exercise can be played back by the virtual fitness trainer by means of the display unit.

8. The fitness device according to claim 1, wherein by the communication equipment a fitness exercise demonstrated by a virtual fitness trainer can be retrieved, in particular via the Internet, and/or data of a user can be retrieved for evaluating a fitness exercise performed by the user.

9. The fitness device according to claim 1, wherein the identification means is equipped and provided to identify a user by means of an entered user ID and a password and/or by means of a contactless scanning of an identification element, in particular a transponder, carried by the user.

10. A system with a plurality of fitness devices according to claim 1, wherein the individual fitness devices each are equipped to direct an identified user after termination of a fitness exercise performed at a first fitness device to a second fitness device at which a succeeding fitness exercise is to be performed by the user.

11. The system according to claim 10, wherein the individual fitness devices are electronically coupled with each other, so that data on an identified user, who has performed a fitness exercise at the first fitness device, are available at the second fitness device.

12. The system according to claim 10, wherein the system is equipped and provided to automatically perform an assignment to the second fitness device in dependence on
  a determined extent of the deviations of the motions performed by the user from the stored motion sequences during the fitness exercise at the first fitness device and/or
  the identified user and/or
  fitness data of the identified user, in particular the blood pressure and/or the heart rate.

13. The system according to claim 10, wherein the fitness devices are arranged such that each fitness device forms an individual station of a circuit training for an identified user.

14. A method for automatically checking for the correct performance of a fitness exercise, with the following steps:
  providing a fitness device with at least one sensor equipment, one display unit, one identification means, one computer unit and one communication equipment,
  recording and digitizing a fitness exercise performed by a real fitness trainer, so that the fitness exercise can be played back by a virtual fitness trainer by means of the display unit,
  identifying a particular user from a list of users stored in the computer unit by means of the identification means,
  transmitting data from a user to the computer unit by means of communication equipment and transmitting a personal fitness plan of the identified user to the computer unit via the communication equipment,
  displaying motion sequences of the recorded and digitized fitness exercise by the virtual fitness trainer by means of the display unit on the basis of the personal fitness plan,
  contactless detection of the motions of a user utilizing the fitness device by means of the sensor equipment, and
  forwarding signals generated by the sensor equipment on the basis of the motions of the user to the computer unit,
  generating a virtual image of the user by the computer unit on the basis of the signals received from the sensor equipment and displaying the virtual image of the user by means of the display unit in real time,
  performing a comparison with reference to the signals received from the sensor equipment by the computer unit concerning the extent to which the detected motions performed by the user for the fitness exercise deviate from the motion sequences stored in a memory of the computer unit and demonstrated by the virtual fitness trainer, in order to check for the correct performance of the fitness exercise by the user, and
  displaying deviations of the motions performed by the user from the stored motion sequences by means of the display unit in real time for the user performing the fitness exercise,
  wherein the communication equipment is further provided to store user-relevant data including the personal fitness plan on a central server or on a storage medium of the user removable from the fitness device so that the user can use the user-relevant data on different IT input devices independent of the fitness device and can retrieve, view, process and execute its personal fitness plan by means of an IT input device or another fitness device.

* * * * *